(12) United States Patent
Hanson, III

(10) Patent No.: US 6,620,109 B2
(45) Date of Patent: *Sep. 16, 2003

(54) METHOD AND SYSTEM OF DIAGNOSING INTRAPULMONARY INFECTION USING AN ELECTRONIC NOSE

(75) Inventor: C. William Hanson, III, Radnor, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/227,181

(22) Filed: Aug. 23, 2002

(65) Prior Publication Data

US 2003/0078511 A1 Apr. 24, 2003

Related U.S. Application Data

(62) Division of application No. 09/719,504, filed on Feb. 9, 2001, now Pat. No. 6,461,306.
(60) Provisional application No. 60/089,232, filed on Jun. 15, 1998.

(51) Int. Cl.[7] ................................................ A61B 5/00
(52) U.S. Cl. ......................... 600/532; 73/23.3; 422/84
(58) Field of Search .......................... 600/532; 73/23.3; 422/84

(56) References Cited

U.S. PATENT DOCUMENTS

| | | |
|---|---|---|
| 4,887,455 A | 12/1989 | Payne et al. |
| 5,675,070 A | 10/1997 | Gelperin |
| 5,697,326 A | 12/1997 | Mottram et al. |
| 5,698,089 A | 12/1997 | Lewis et al. |
| 5,787,885 A | 8/1998 | Lemelson |
| 5,788,833 A | 8/1998 | Lewis et al. |
| 5,807,701 A | 9/1998 | Payne et al. |
| 5,891,398 A | 4/1999 | Lewis et al. |
| 6,040,189 A | 3/2000 | Buehler |
| 6,042,788 A | 3/2000 | DeWit et al. |
| 6,129,680 A | 10/2000 | Mottram |

FOREIGN PATENT DOCUMENTS

| | | |
|---|---|---|
| WO | WO 98/39470 A1 | 11/1998 |

OTHER PUBLICATIONS

Hanson, C. W., Steinberger, H. A.: Anesthesiology 1997;87:A269.

Parry, A. D., et al: Leg ulcer odour detection identifies β–haemolytic streptococcal infection. Journal of Wound Care. 1995; 4:404–6.

"Electronic Nose Sniffs Out Infections," web site printout of news article dated Oct. 22, 1997, printout from web site http://pslgroup.com/dg/3ee56.htm, printout date: May 25, 1999, 3 pages.

*Primary Examiner*—Robert L. Nasser
(74) *Attorney, Agent, or Firm*—Akin Gump Strauss Hauer & Feld, L.L.P.

(57) ABSTRACT

The presence of a pathologic process in a lung of a mammal is detected by applying exhaled gas of a mammal to an electronic nose. Data derived from the electronic nose is used to determine whether a pathologic process is present in the lung of the mammal. The pathologic process may be a lung infection such as pneumonia.

28 Claims, 15 Drawing Sheets

METHOD AND SYSTEM OF DIAGNOSING INTRAPULMONARY INFECTION USING AN ELECTRONIC NOSE

CROSS-REFERENCE TO RELATED APPLICATIONS

This application claims the benefit of U.S. Provisional Application No. 60/089,232 filed Jun. 15, 1998 entitled "METHOD AND APPARATUS FOR DIAGNOSIS OF INTRAPULMONARY INFECTION AND OTHER INFECTIONS AND DISEASES".

This application is a division of U.S. application Ser. No. 09/719,504 filed Feb. 9, 2001 now U.S. Pat. No. 6,461,306 (35 U.S.C. § 371 date) entitled "DIAGNOSING INTRAPULMONARY INFECTION AND ANALYZING NASAL SAMPLE," the entire disclosure of which is incorporated herein by reference.

BACKGROUND OF THE INVENTION

The sense of smell has long been used as a diagnostic tool by medical clinicians. Because of its subjectivity and the lack of correlative monitors, smell, as a diagnostic tool, has never achieved significant prominence in modern medicine. "Electronic noses" or "electronic olfactory sensors" have recently been developed to provide objective measurements and analysis of aromas. One particular "electronic nose" which has achieved some commercial success, primarily in the area of quality control and environmental monitoring in particular industries such as the beverage, flavor, perfume and certain aspects of the food industries, is manufactured by Aromascan, Inc. of Hollis, N.H. The Aromascan product uses changes in an electrical property (specifically, impedance or resistance) of sensors in a sensor array made of a layer of a semi-conducting organic polymer, when exposed to particles in a gas for aroma analysis. The Aromascan product is disclosed in U.S. Pat. No. 4,887,455 (Payne et al.), the disclosure of which is incorporated herein by reference. The use of the Aromascan product permits the characterization and digital representation of aromas for the measurement, recording and objective analysis of aromas. In this manner, the Aromascan product emulates the performance of the human nose with discrimination, sensitivity and, most importantly, objective reproducibility. Details concerning the structure and operation of the Aromascan product are available from Aromascan and the above-cited patent.

When using the Aromascan product, an aroma sample is exposed to the sensor and provides an aroma "fingerprint" which may be compared to another aroma finger print or other base data to provide a characterization of the sensed aroma. The Aromascan product outputs data regarding the aroma sample in the following formats:

1. A bar chart/histogram which shows the response of each sensor in the sensor array to the aroma presented to the array. Both the line pattern and the bar chart will be different for each odor thereby giving each odor a unique fingerprint.

2. Overlaid bar charts which highlight the average degree of differences between two samples at each individual sensor in the array.

3. 2-dimensional or 3-dimensional "AromaMaps." The plural sensor data may be reduced to one point on a 2-D or 3-D plot or map which represent normalized histogram values. These plots allow for sample-to-sample comparisons. Samples which are similar to each other form populations or clusters on the map. Different aromas should fall within different clusters.

AromaMaps are one form of a "multi-dimensional map" for representing the sensor data and may be referred to generically as a principle component analysis (PCA) map. Another form of a multi-dimensional map which may be used for representing the sensor data is a Sammon map, such as shown in FIG. 5 of U.S. Pat. No. 5,807,701.

Two conventional sampling techniques for exposing an aroma to an electronic nose sensor include static headspace analysis and flow injection analysis. In static headspace analysis, a headspace above the sample is defined which becomes saturated with the odor. The odor is then pumped across the sensor. In flow injection analysis, a known gas is constantly pumped across the sensor. Next, a known concentration of the gas to be sampled is injected into the fluid stream before the sensor.

Electronic noses and methods of using electronic noses are further described in U.S. Pat. No. 5,675,070 (Gelperin); U.S. Pat. No. 5,697,326 (Mottram et al.); U.S. Pat. No. 5,788,833 (Lewis et al.); U.S. Pat. No. 5,807,701 (Payne et al.); and U.S. Pat. No. 5,891,398 (Lewis et al.), the disclosures of which are incorporated herein by reference.

U.S. Pat. No. 5,807,701 (Payne et al.), assigned to Aromascan PLC, discloses an in vitro method for identifying a microorganism, and particularly, vapors associated with the bacteria *Staphylococcus aureus, Escherichia coli* and Group A beta-haemolytic streptococci. In the method, the sample is in a Petri dish or like laboratory culture dish and undergoes culturing and growth before sampling occurs. A combination of static headspace analysis and flow injection analysis is used to perform the sampling.

U.S. Pat. No. 5,697,326 (Mottram et al.) discloses an examination device in the form of an open-top vessel which is used in conjunction with an electronic nose to sample odors emanating from the teat of a ruminant animal. The sampling is performed prior to milking to determine if the animal should be milked, cleaned or examined further. The patent also states that the examination device may be used to sample exhaled breath from the respiratory tract of a ruminant animal to determine selected conditions of the animal, such as oestrus (estrus) and ketosis. No data is presented to support these uses.

The diagnosis of pulmonary infections in mammals such as humans is a time-consuming, resource intensive process and sometimes inaccurate process. A chest x-ray does not necessarily provide an accurate indication of the presence or absence of an infection. Bacterial culture results typically take one to three days. During the test result waiting period, patients may be given powerful, often unneeded antibiotics which foster the growth of resistant bacteria.

Accordingly, there is an unmet need for a fast, accurate and inexpensive process for diagnosing pulmonary infections. The present invention fulfills this need.

Cerebrospinal fluid (CSF) is a clear fluid that circulates in the space surrounding the spinal cord and brain. CSF bathes, cushions and protects the spinal cord and brain. CSF flows through the skull and spine in the subarachnoid space.

The sinuses of a healthy patient contain mucus produced by sino-nasal mucosa and does not contain CSF. The sinuses of a patient who has a skull-base defect (either congenital, iatrogenic or trauma-induced) may contain CSF. In such patients, CSF may leak or drain through a skull-base defect into the sinuses and then into the nose. CSF may also drain directly into the nose through a skull-base defect at the olfactory cleft. Since sinus mucus and CSF are both clear fluids, a clinician cannot tell whether a CSF leak exists unless a patient ultimately tests positive for CSF.

In a patient suspected of having a CSF leak, sinus fluid is collected by gravity drip (e.g., the patient leans forward and nasal fluid drains out of the nostril into a vial), pledget sampling, aspiration or other means. A beta-2 transferrin enzyme assay is then conducted on the fluid sample to determine the presence of CSF. Although this test is very accurate, the test requires a relatively large amount of fluid. It is sometimes difficult to obtain a sufficiently large amount of fluid to conduct the test. Also, in many institutions, there can be a turnaround time of 24–48 hours for results. If a patient ultimately tests positive for CSF, the underlying condition or disease which caused the CSF leak may remain untreated unless other obvious signs of the condition, such as meningitis become apparent.

Accordingly, there is an unmet need for a fast, accurate and inexpensive process for detecting whether a fluid sample contains CSF, thereby differentiating CSF from other sinus-related fluids. There is also an unmet need for a testing process which does not require large quantities of fluid. The present invention also fulfills these needs.

BRIEF SUMMARY OF THE PRESENT INVENTION

The present invention provides a method of detecting the presence of a pathologic process in a lung of a mammal. In the method, a sample of exhaled gas collected from the lung of a mammal is applied to an electronic nose. The electronic nose analyzes the sample to determine whether a pathologic process is present in the lung of the mammal.

BRIEF DESCRIPTION OF THE DRAWINGS

The following detailed description of preferred embodiments of the present invention would be better understood when read in conjunction with the appended drawings. For the purpose of illustrating the present invention, there is shown in the drawings embodiments which are presently preferred. However, the present invention is not limited to the precise arrangements and instrumentalities shown. In the drawings.

DETAILED DESCRIPTION OF THE INVENTION

Figure 1:
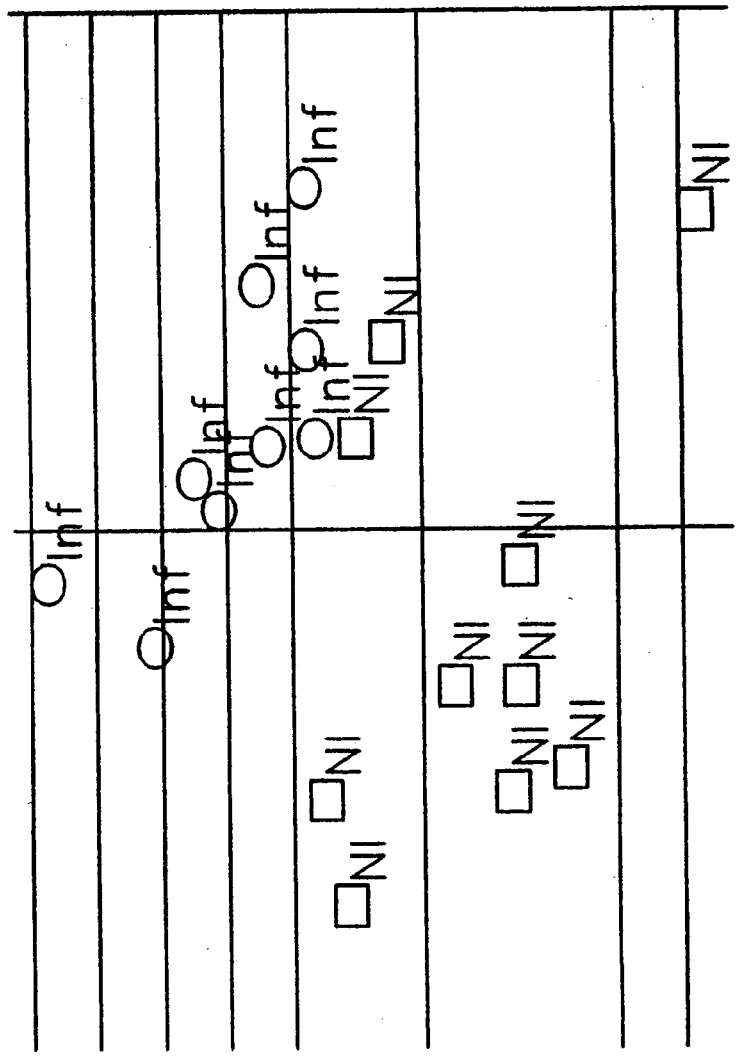
FIG. 1 is a diagram of the results of a test of the present invention for diagnosing pulmonary infection in Example 1 below.

Certain terminology is used herein for convenience only and is not to be taken as a limitation on the present invention.

In the drawings, the same reference letters are employed for designating the same elements throughout the several figures.

Diagnosis of Intrapulmonary Infection Using an Electronic Nose

The present invention uses the Aromascan product or some other "electronic nose" for the purpose of analyzing gases exhaled or otherwise obtained from a patient for the purpose of rapidly determining the presence of pathologic processes in the lung or other parts of the patient resulting in alterations or deviations in the analyzed gases. A "pathologic process" as defined herein is necrosis, hemorrhaging, or an inflammatory process in the lung, such as an infection, along with other disease conditions for which a diagnosis is desired. The present invention is particularly useful in the rapid detection of lung infections and specifically differentiation between lung infiltrates (on chest x-rays) caused by infections versus lung collapse. Currently, such differentiation relies upon cultures which are expensive and time consuming (one to two days). With the present invention, such differentiation can be determined substantially immediately, and without requiring culturing or growing of a sample.

EXAMPLE 1

In one test of the present invention, exhaled gas was collected from the ventilator circuit of nineteen intubated intensive care patients. Ten of the nineteen patients were immediately postoperative and were presumed to be uninfected (control group). Nine of the patients had previously been identified as having positive bacterial cultures as assessed in tracheal aspirates. The exhaled gases from the nineteen patients were analyzed utilizing the Aromascan product with multi-element odor detection in which the exhaled gas was exposed to a twenty-element semiconductor polymer such that volatile molecules from the gas interacted with the polymer, altering the electrical resistance in unique patterns.

FIG. 1 shows the results of the test. In FIG. 1 the ten patients which were presumed to be uninfected were considered to be the controls and are marked with the reference symbols NI. The patients which were known to have been infected are marked with the symbol Inf. As can clearly be seen from FIG. 1 the patients known to be infected are substantially clustered and distinguishable from the uninfected patients.

In a further test, exhaled gas was collected from nineteen intubated intensive care patients. Eight of the patients were immediately postoperative and were presumed to be uninfected (control). Eight of the patients had tracheal cultures positive for various bacteria species (*A. bazimanii, E. coli* and *S. aureus*) and three of the patients had positive cultures for *C. albicans* in tracheal aspirates. Again, the exhaled gases were analyzed utilizing the Aromascan product with multi-element odor detection in which the gases were exposed to a 32 element semi-conducting polymer.

Figure 2:
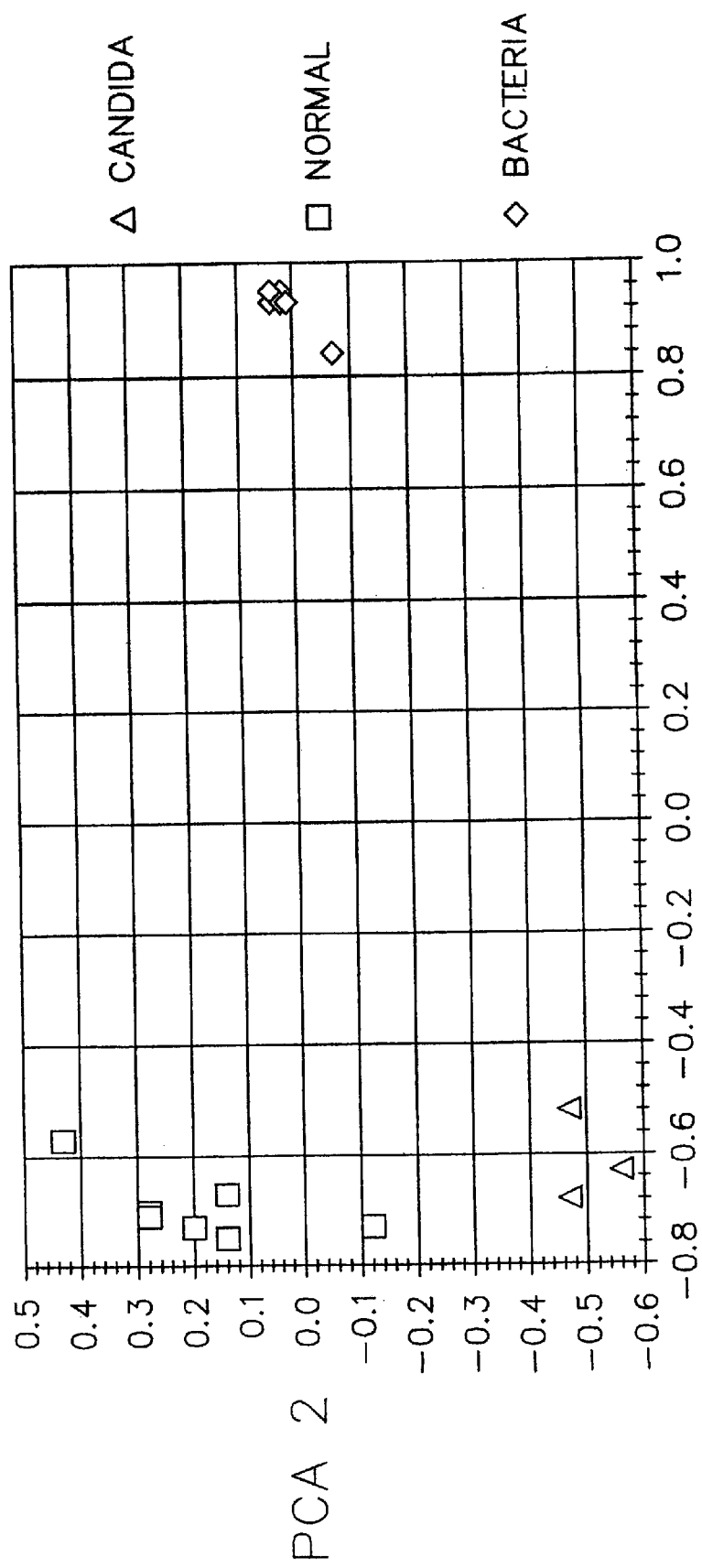
FIG. 2 is a diagram of the results of another test of the present invention for diagnosing pulmonary infection in Example 1.

FIG. 2 shows the results of the analysis in which the normal or uninfected patients are indicated with boxes, the patients infected with *C. albicans* (the most frequent agent of candidiasis) are indicated with triangles and the patients having a bacterial infection are indicated with diamonds. Again, as indicated by FIG. 2, there is a clear demarcation between the uninfected or control patients and the patients known to be infected with a microorganism.

In a third test, exhaled gas was collected from the ventilator circuit of ten intubated intensive care patients. Eight of the patients were immediately postoperative and were presumed to be uninfected (control). Two of the patients had positive cultures for *C. albicans* in tracheal aspirates. The exhaled gases were analyzed utilizing the Aromascan product with multi-element odor detection utilizing a 32 element semi-conducting polymer such that volatile molecules from the gas interacted with the polymer for altering the polymer resistance in unique patterns. This study also demonstrated a discernible mapping of the results between the control patients and the infected patients.

After an extensive sampling of a large number of patients and characterization by the Aromascan of the breath exhaled by such patients, a database is employed for the characterization of the expected output for a variety of known diseases, infections or other ailments.

Figure 3:
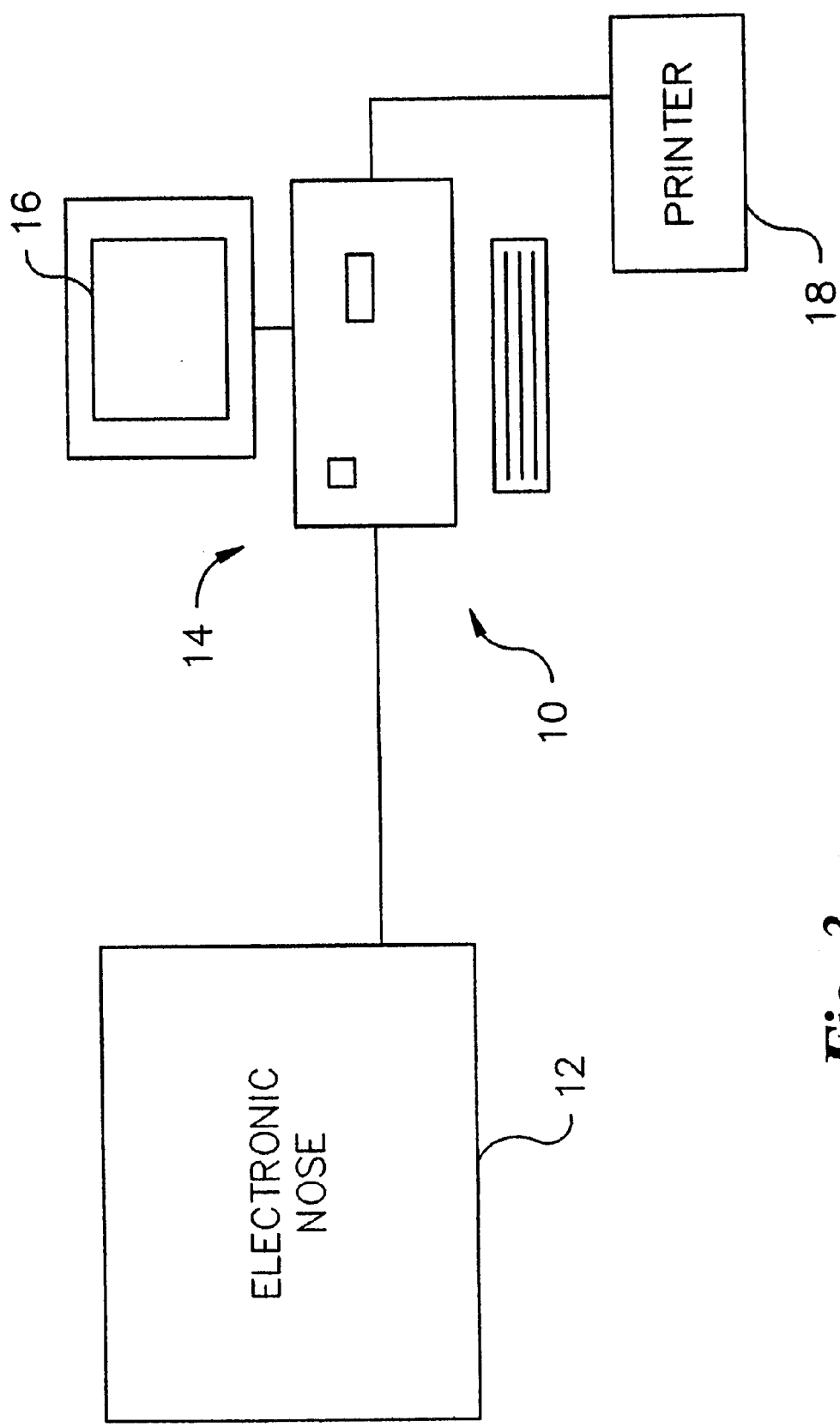
FIG. 3 is a schematic functional block diagram of one embodiment of the invention.
Figure 4:
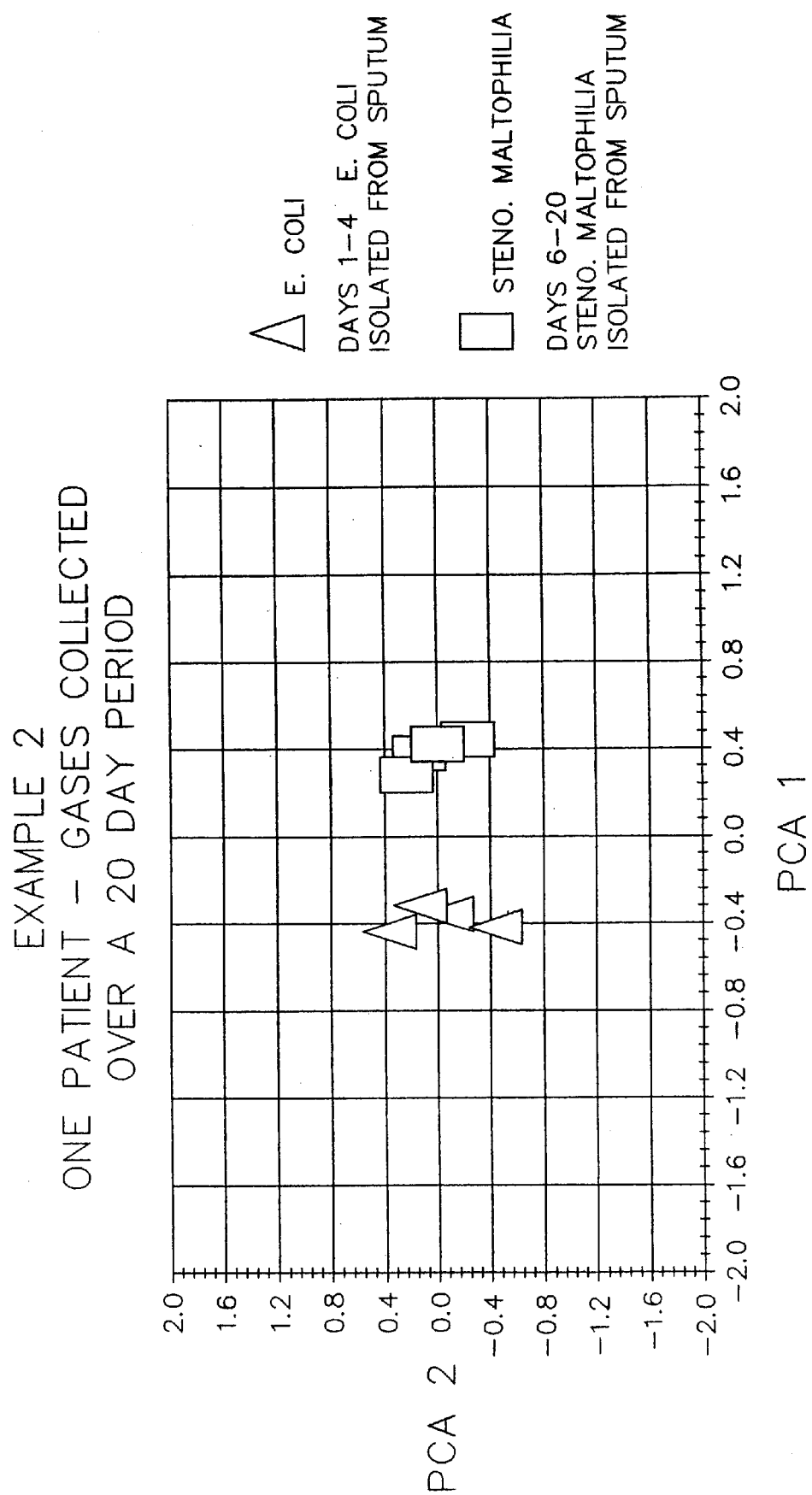
FIGS. 4–8 are multi-dimensional maps of patient gas samples taken for detecting lung infections.
Figure 5:
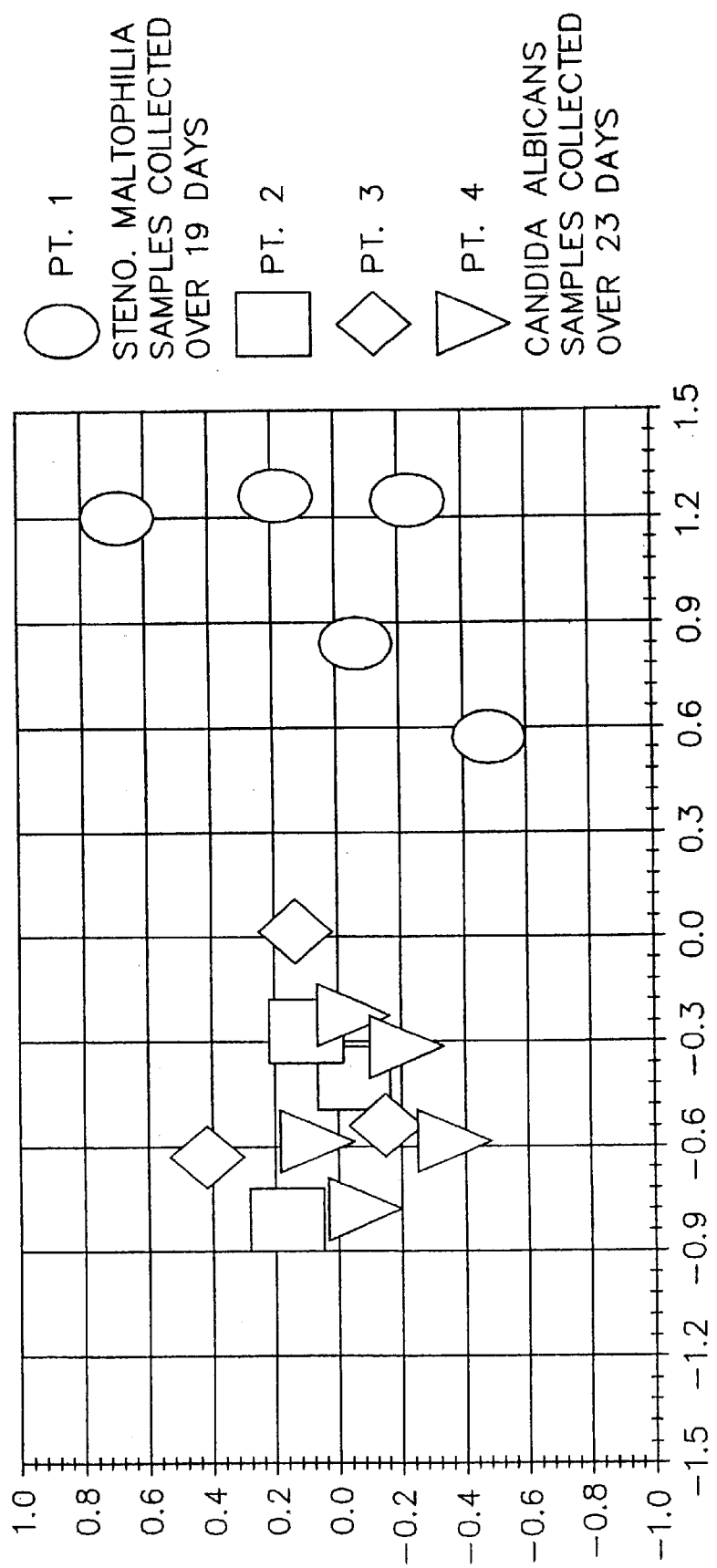
Figure 6:
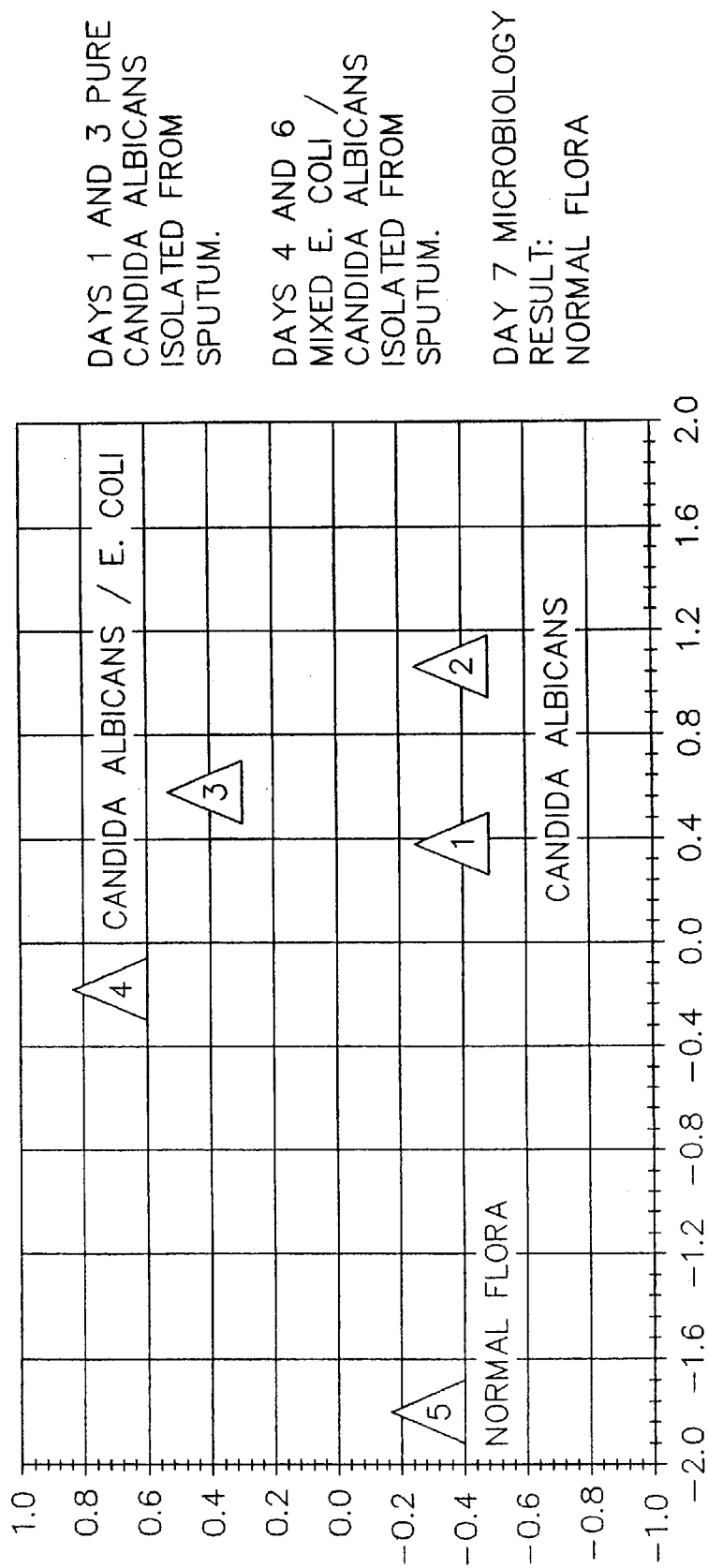
Figure 7:
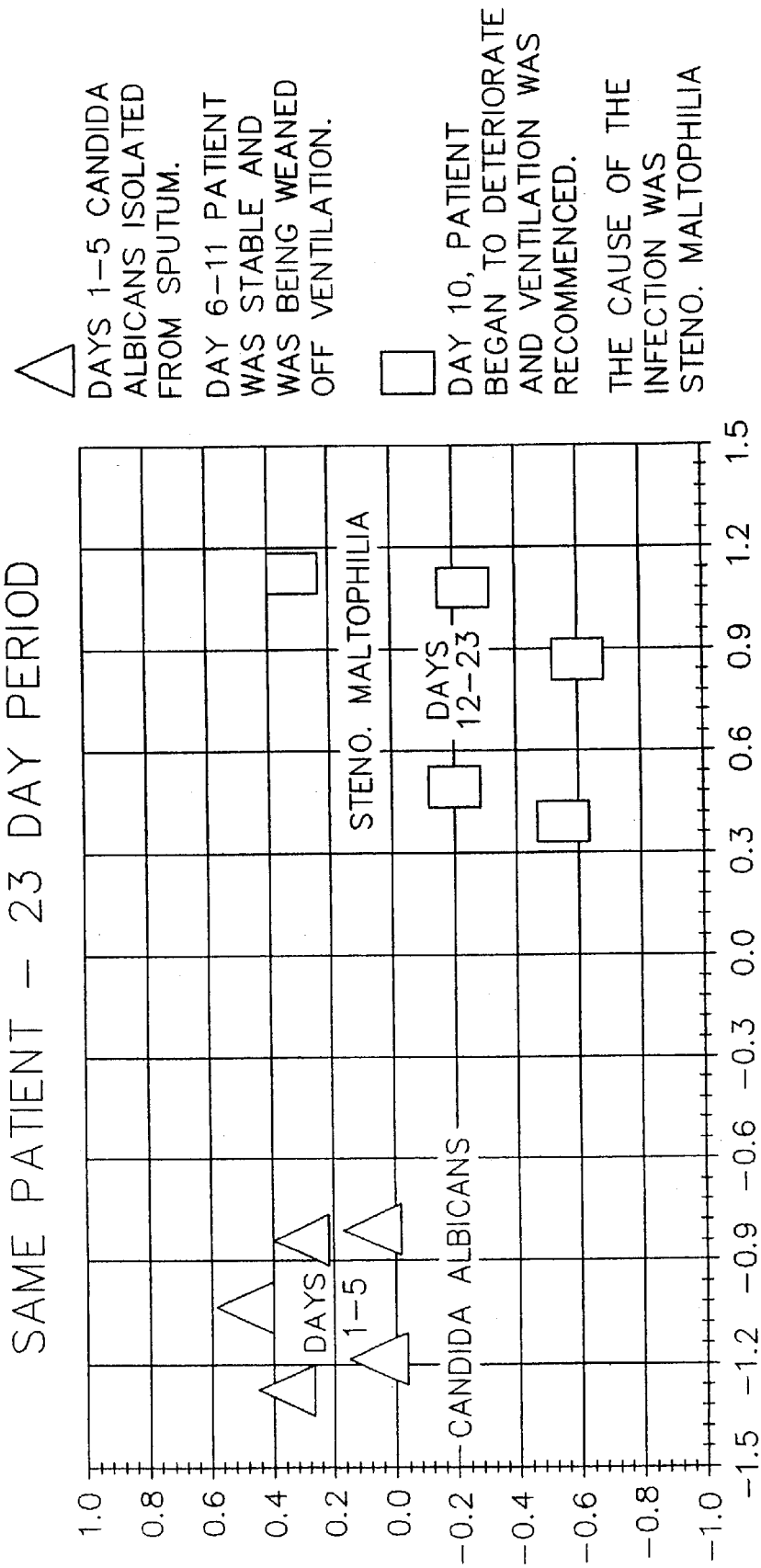
Figure 8:
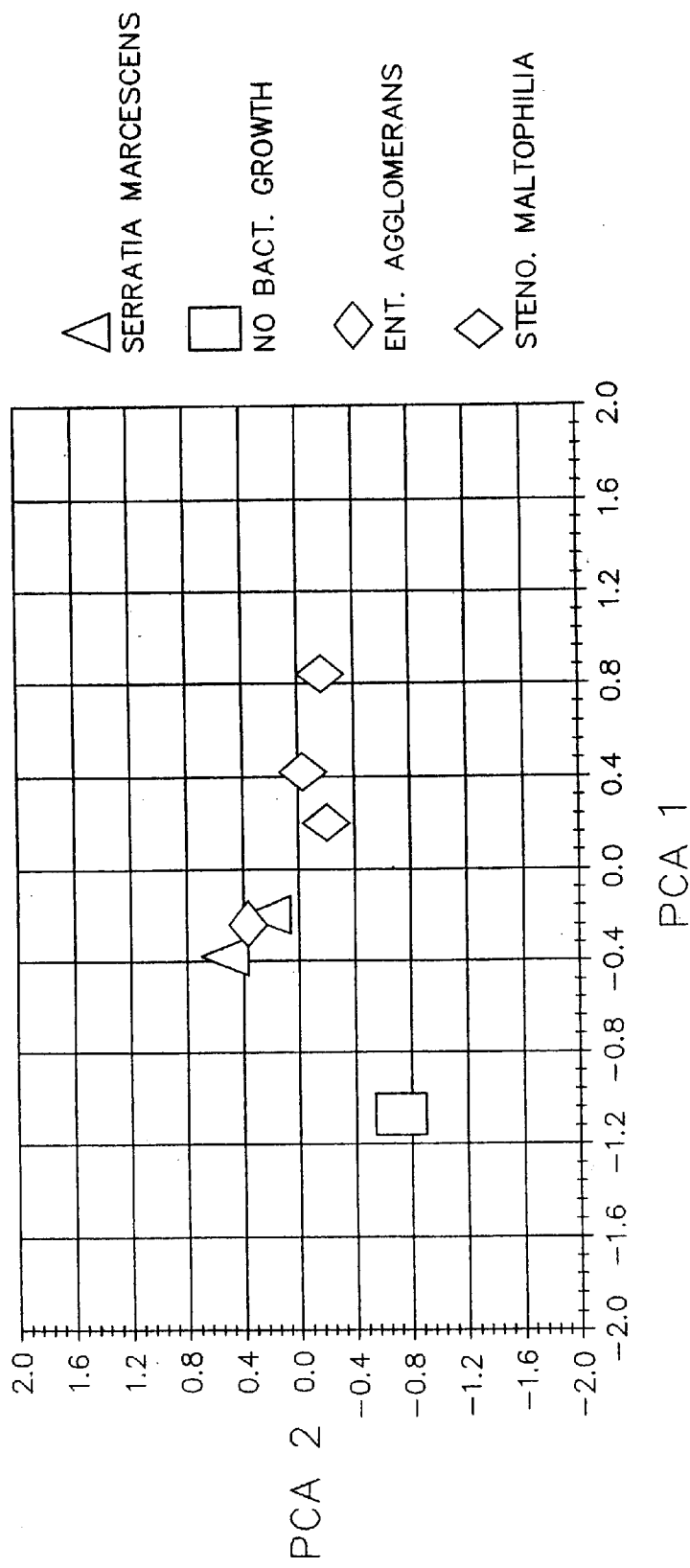

FIG. 3 is a block diagram representation of a system 10 for performing such analysis. The system 10 includes an electronic nose 12 such as the Aromascan product or some other product performing the same function. The electronic nose 12 is connected to a personal computer 12 or any other suitable computer or electronic device. In the illustrated system 10, the personal computer includes a memory (not shown) having a database which stores a significant amount of patient information which was obtained as a result of extensive patient testing and analysis to identify the expected output in the form of a unique or repetitive pattern from the Aromascan product for various infections, diseases, conditions and the like. The computer 14 also includes software to permit the computer 14 to receive the output data from the electronic nose 12 and, utilizing the information from the database, make appropriate comparisons and generate a diagnosis or suggestion regarding an infection, disease, condition or the like which is likely to be present in the patient. The diagnosis may be presented to the user on the computer screen 16 or may be provided to a printer 18 for hard copy output.

EXAMPLES 2–6

FIGS. 4–8 provides additional patient data which shows distinguishable clusters for patient samples which have different types of lung infections and for uninfected patient samples. FIGS. 4–8 are self-explanatory and thus are not further described herein.

The samples collected in Examples 1–6 used a vapor form of expired air from the patients, and did not use condensate of the vapor form.

EXAMPLE 7

In example 7, testing was done on condensate from the patients since it is known that condensate contains volatiles from the expired air. Test equipment included a standard Aromascan A32S/CEM using a temperature controlled 25 ml sample vial and a carrier gas.

The protocol for obtaining and testing samples in Example 7 was as follows:

1. Collect 10 ml of condensate from a collection vessel inserted just before the ventilator catch pot using a plastic syringe.

2. Extract 250 µl of condensate into the syringe.

3. A reference signal was set up for the Aromascan A32S/CEM by passing approximately 90 ml/min of carrier gas through a sample vial containing 2 ml of 10% sodium hydroxide (NaOH) held at 33° C.

4. At 60 seconds into the run, the syringe containing 250 µl of condensate is injected into the sample vial.

5. At 180 seconds into the run, the sample vial is replaced with a fresh vial of 2 ml of 10% NaOH to act as a wash and to become the next sample vial.

Figure 9:
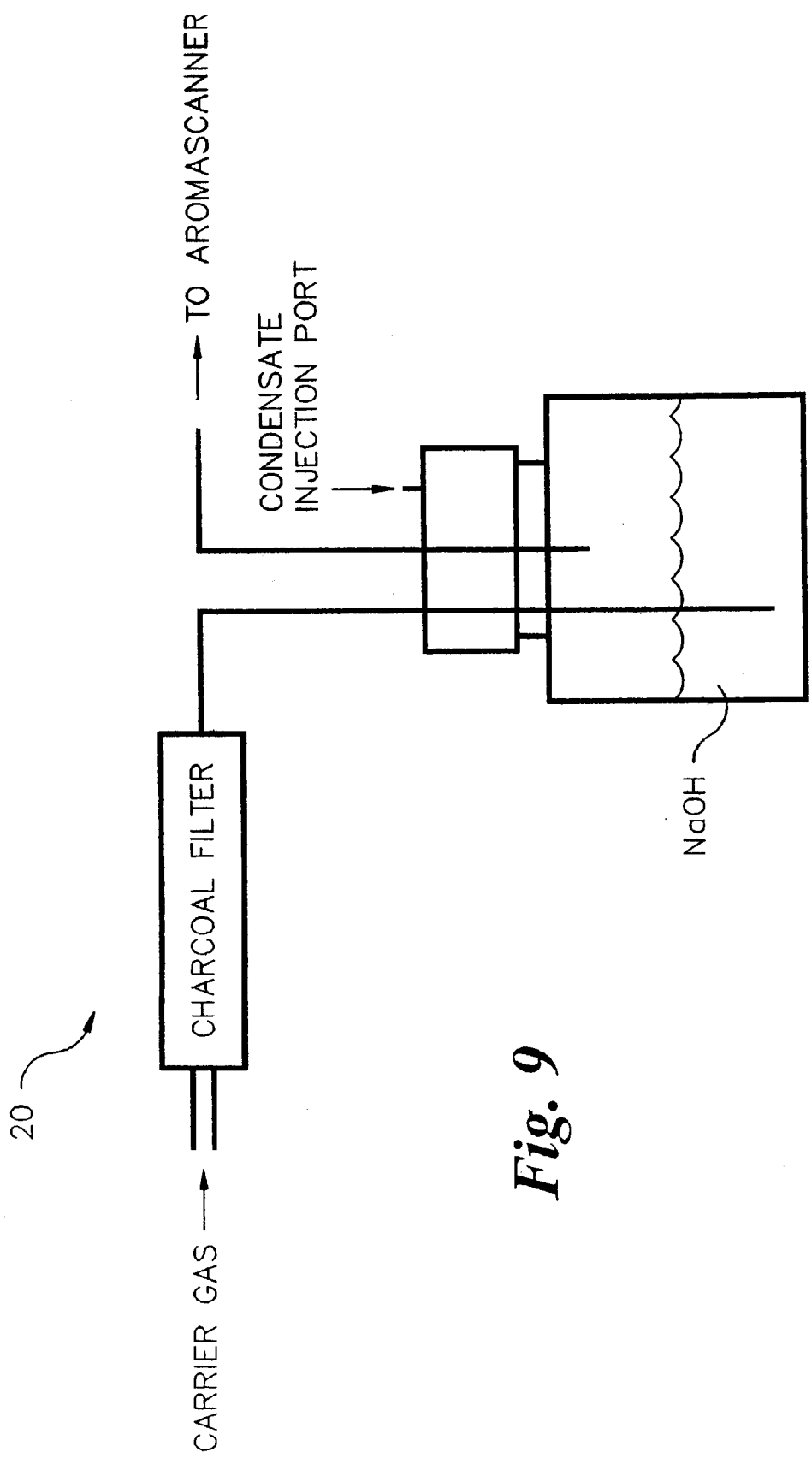
FIG. 9 is a schematic diagram of configurations for obtaining and testing patient gas samples in accordance with the present invention.

FIG. 9 is a schematic diagram of a configuration 20 for the above-described protocol.

Test process: Exhaled gas was collected from the ventilator circuit of intubated patients to determine if pathologic processes could be detected. More than 60 samples were measured from 17 different patients over three days. Each patient was prospectively rated on an integer scale from 1–5, 1 being least likely to have a lung infection, 5 being very likely to be clearly infected.

Figure 10:
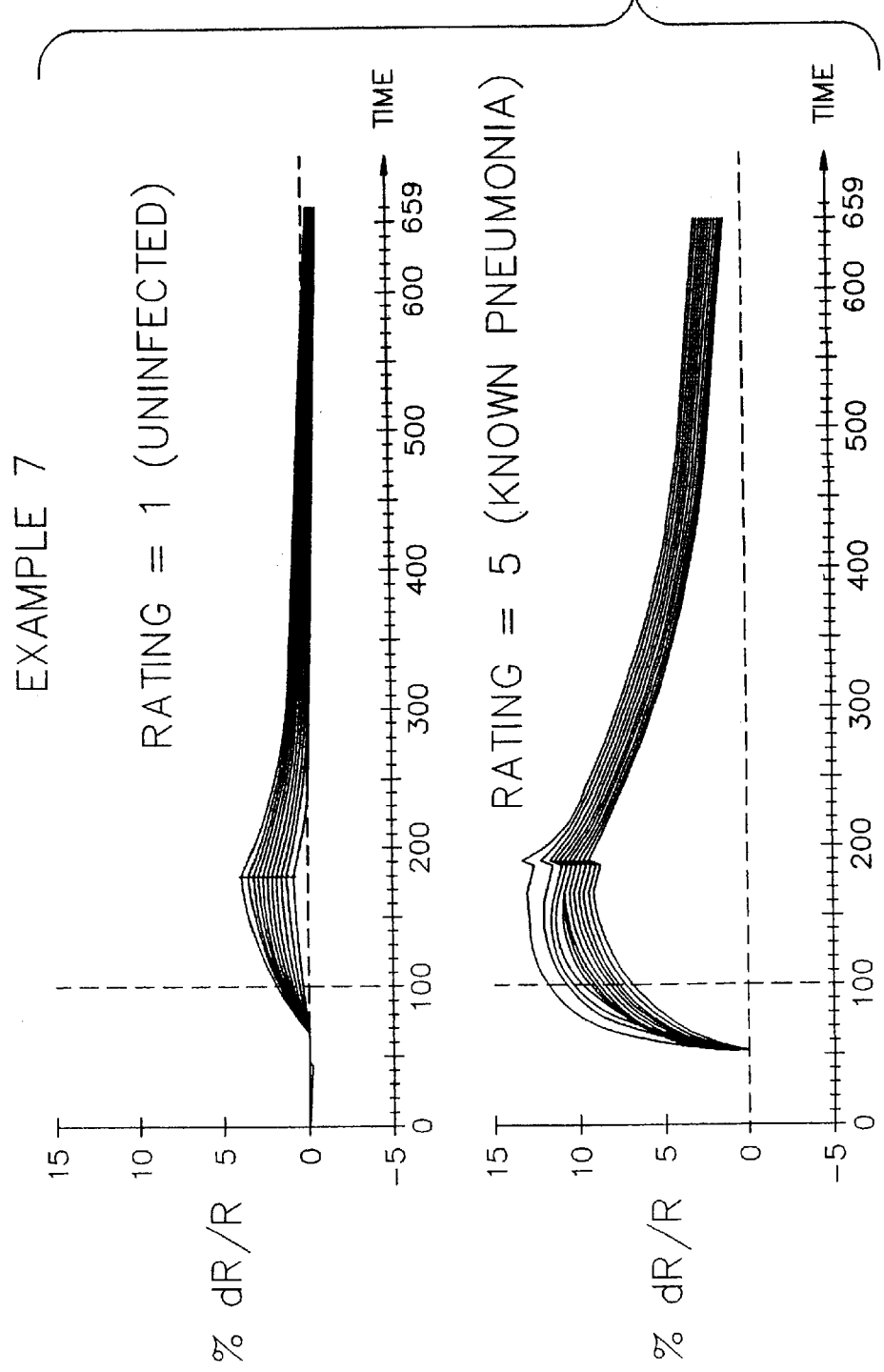
FIG. 10 shows line patterns generated by an electronic nose for patient gas samples using a condensate of the expired gas.

One rating scheme which is suitable for use with the present invention and which was used in the examples described herein is as follows:

1=fresh post-op, presumed uninfected
2=several days post-op, presumed uninfected
3=several days post-op, suspicious chest x-ray (CXR)
4=chest x-ray shows infiltrate, suspicious sputum
5=chest x-ray shows infiltrate, sputum positive for infection FIG. 10 shows typical sensor acquisition profiles for samples rated 1 and 5. From the data in FIG. 10, it can be concluded that the intensity of response, rather than pattern differences, was the dominant factor in discriminating the samples.

Figure 11:
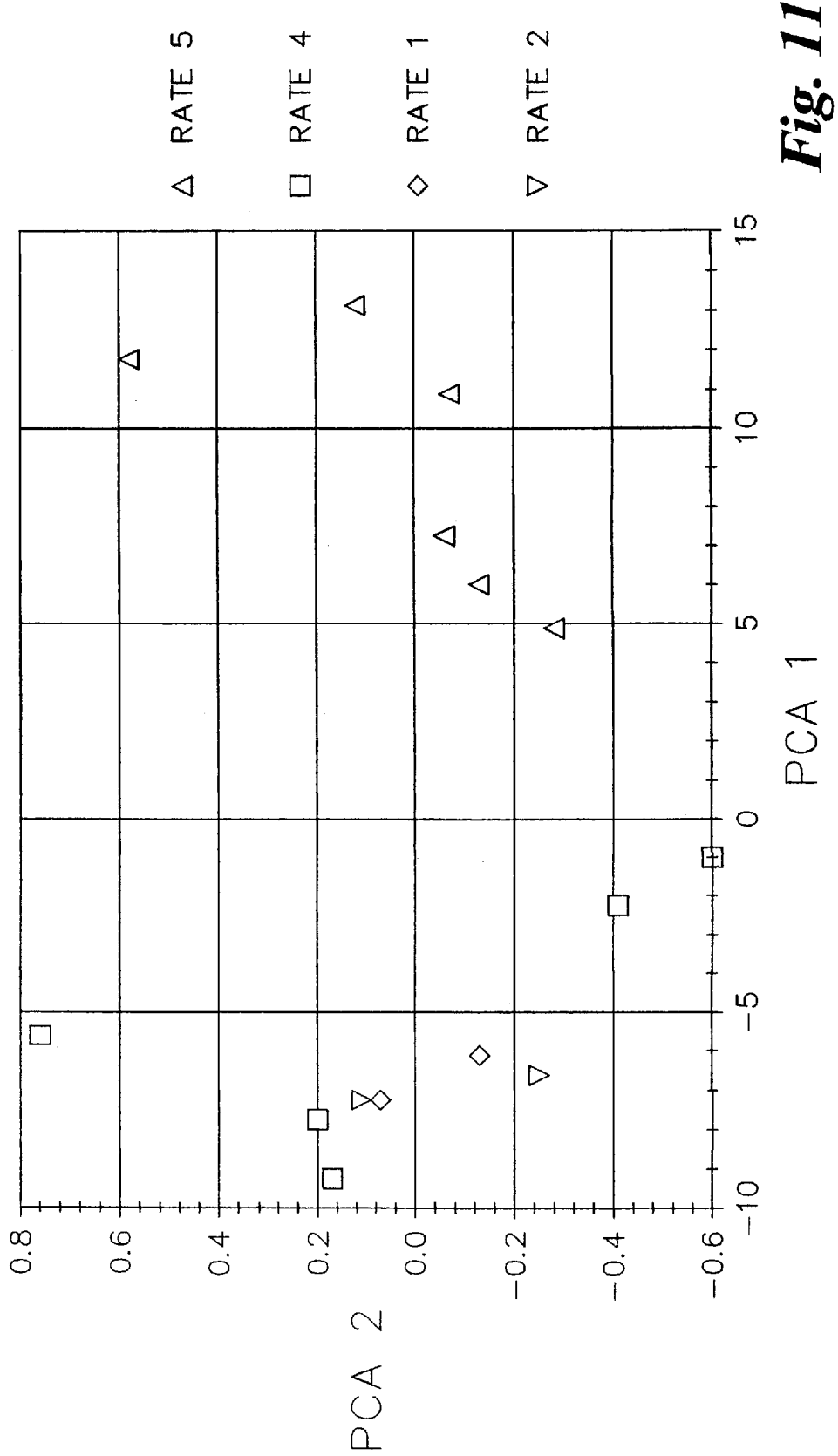
FIGS. 11 and 12 are multi-dimensional maps of patient gas samples taken for detecting lung infections using a condensate of the expired gas.

FIG 11 is a map based on an intensity pattern for the time slice of 70–100 seconds from Day 1 samples only, from six patients with repeats, some being separate aliquots of the same sample. FIG. 11 shows that the low and high rated groups have clear separations. That is, the patients who were prospectively rated as being unlikely to be infected formed a cluster which is clearly separate from the cluster formed by the patients who were prospectively rated as being clearly infected.

Referring to FIG. 11, when the PCA2 scale is considered, the discrimination is along PCA1. That is, the most likely infected patients (i.e., rating=5) are to the right with good separation from the other ratings. The three #4 ratings on the left-hand side are separate samples from the same patient who was subsequently re-rated as a 2.

Figure 12:
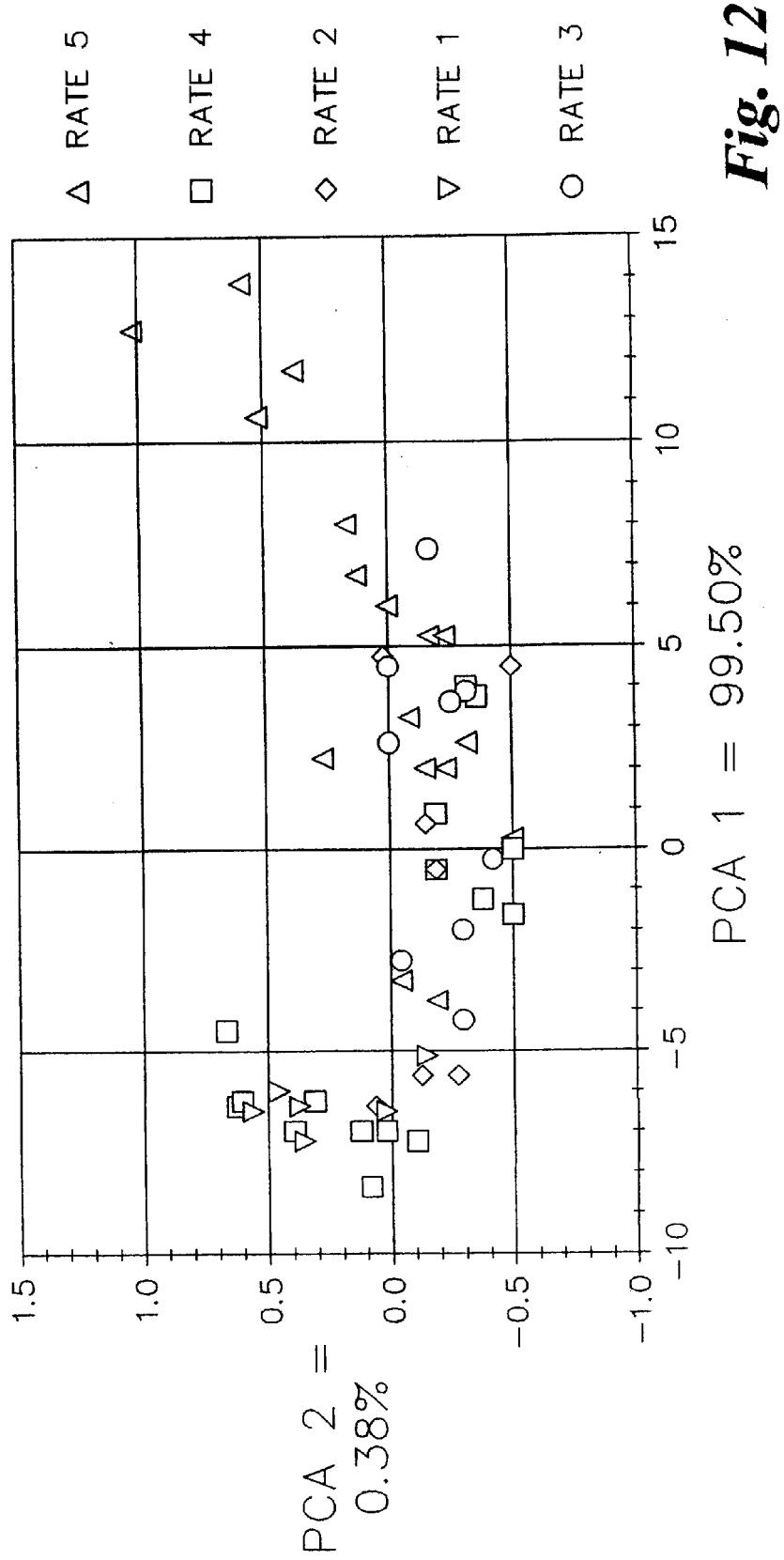

FIG. 12 shows a map of the data for days 1–3. The map now becomes more cluttered and confusing but the basic PCA1 discrimination holds. However, an unknown patient at position 0,0 on this map could be rated anywhere from 1–5. Other raw data analysis and display methods (metrics) may provide better predictions of the patient rating. Other metrics include (1) average of intensity pattern, (2) sum of intensity pattern (a crude approximation to area under curve), and (3) single sensor response.

Patient samples may be collected and analyzed at the patient bedside wherein the gas samples or their condensates are flowed either directly into the electronic nose or from the ventilator circuit into the electronic nose. Alternatively, the gas samples or their condensates may be collected in a transport sample bag (e.g., Tedlar® bag) and delivered to a remote location for measurements by the electronic nose.

The test results described above demonstrate that intrapulmonary infections can be predicted using data output by an electronic nose. For example, when using a 2-dimensional map or 3-dimensional map, cluster analysis can be used to compare data of a patient with an unknown condition to cluster data of patients having known conditions (i.e., infection/no infection).

From the foregoing description it can be seen that the present invention comprises a method and apparatus for aroma analysis of gas from the lungs or elsewhere on a patient for the purpose of identifying infections, conditions, or diseases.

Method of Detecting Whether a Sinus Sample Contains Cerebrospinal Fluid Using an Electronic Nose Testing Method Testing for the results shown in FIGS. 13 and 14 discussed below was performed on samples of serum and CSF from a plurality of patients. That is, multiple paired serum and CSF samples were obtained. Samples of both fluids were collected using conventional techniques. The samples were typically 1 ml or less and were held in a plastic syringe and refrigerated until they were ready for testing. Sample analysis was performed using the condensate process described above, except that 100 µl sample volumes were used to conserve the minimal sample.

RESULTS

Inspection of the acquisition files showed a clear intensity difference between the CSF and serum samples for all sets, wherein the CSF showed the lower intensity.

Figure 13:
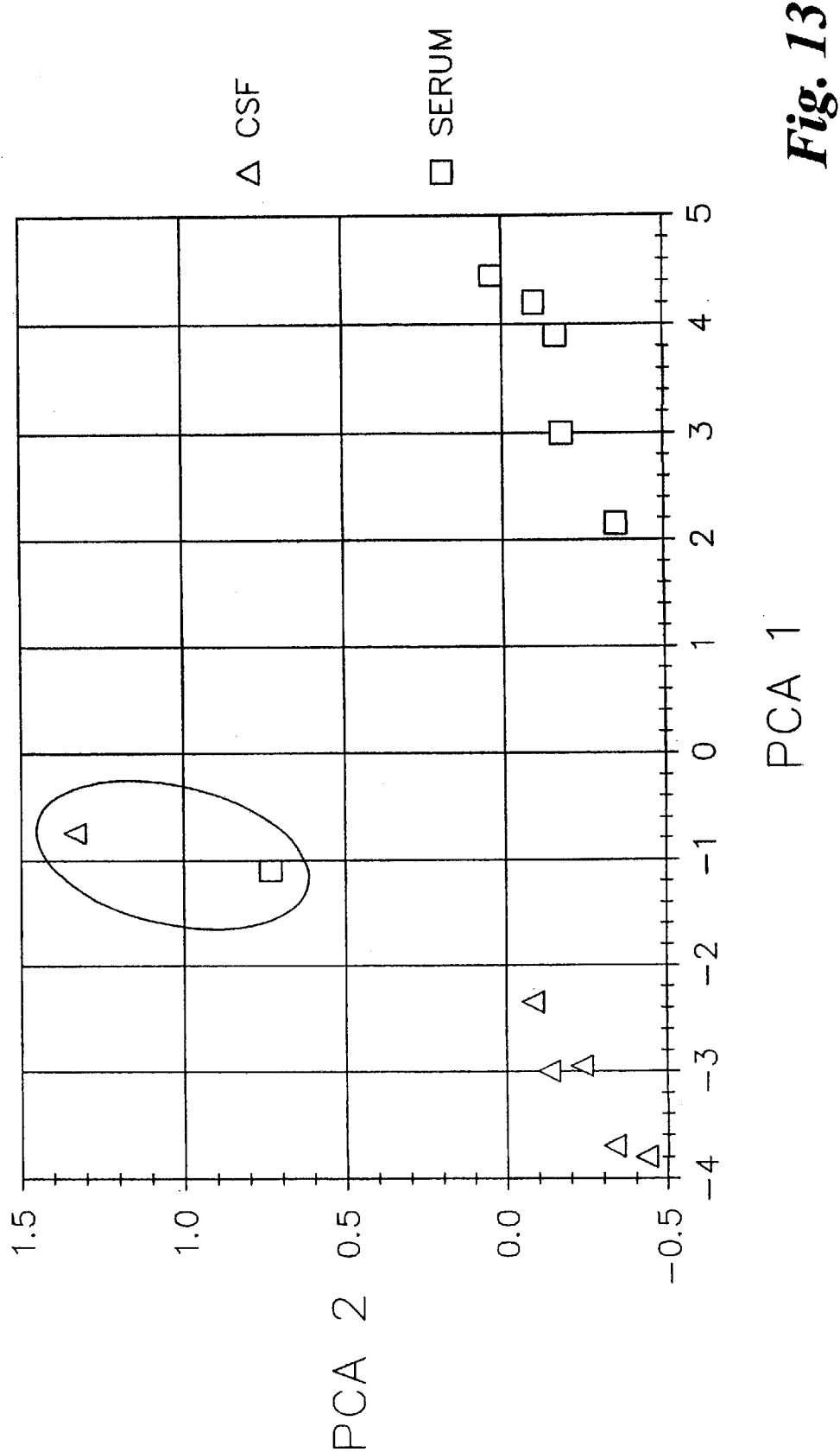
FIGS. 13–15 are multi-dimensional maps of patient fluid samples taken for detecting CSF in the fluid samples.

FIG. 13 is a map of the first sample set results which are from six patients. The two points which are close together (shown circled) are from the same patient. Possible explanations for these two points are contamination/mixture of the two samples. Except for these two points, the serum samples and CSF samples form clearly defined clusters.

Figure 14:
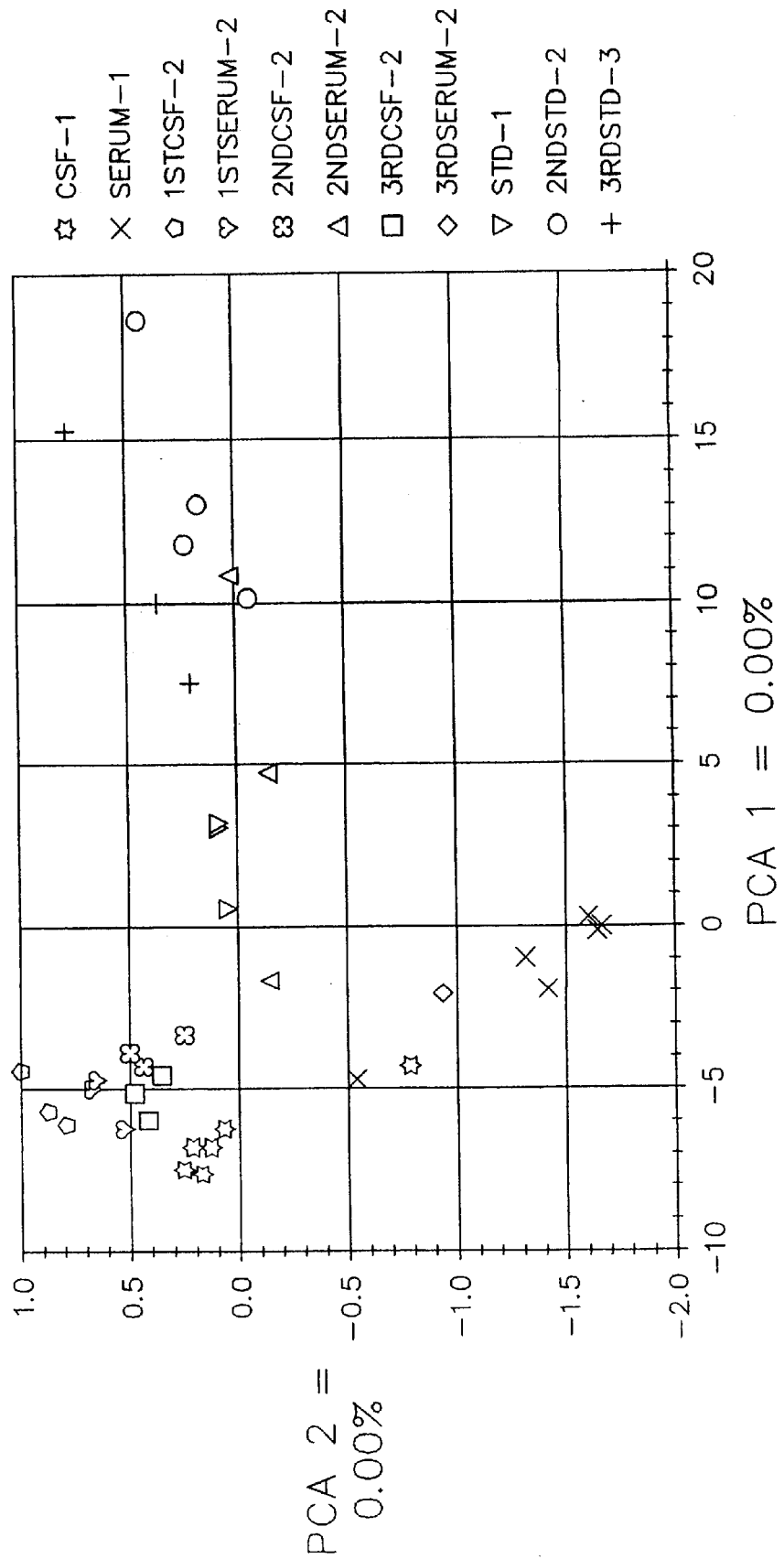

FIG. 14 is a map of the data from a second set of samples, plus calibrants (std's 1–3) from nine patients (the six patients in FIG. 13 and three additional patients).

Figure 15:
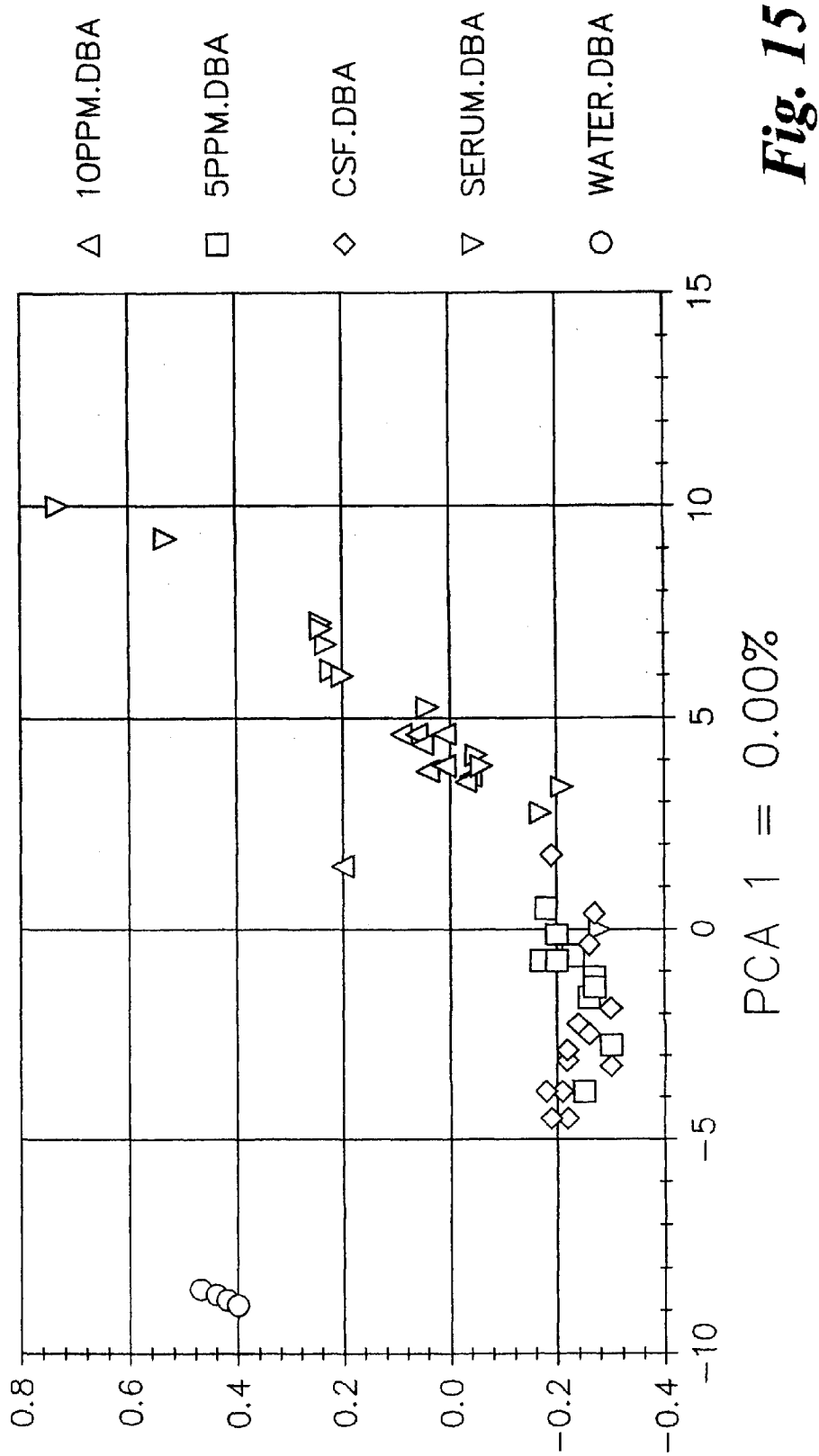

FIG. 15 is a map of the data from a third set of samples from thirteen patients (the nine patients in FIG. 14 and four additional patients).

CONCLUSIONS

The results in FIGS. 13–15 show that CSF may be differentiated from serum. The testing used to obtain the results in FIGS. 13–15 used serum as a control. A similar differentiation should be expected if mucus is used as a control. In a clinical setting, the following procedure should be performed to detect CSF leaks:

1. Collect a sinus or nasal sample, or a "suspected CSF" sample using any of the techniques described in the background section.

2. Apply the sample to an electronic nose using any of the conventional techniques described above (e.g., vapor process using static headspace analysis or flow injection analysis, or condensate process);

3. Analyze the sensor output signal using any of the conventional techniques described above to determine if CSF is present. For example, when using a 2-dimensional map or 3-dimensional map, cluster analysis can be used to compare data of a patient with an unknown condition to cluster data of patients having known conditions (i.e., CSF present/no CSF present, only mucus, serum or both are present).

It should be understood that although in connection with the present invention the Aromascan product is discussed, electronic noses of the type discussed above may be available from one or more other sources. Accordingly, the present invention is not limited to the use of the Aromascan product. When using the Aromascan product, principal component analysis is employed to create the 2-dimensional plots. The output signals produced by the array of individual sensors in the Aromascan product are referred to herein as a "sensor output signal" of an electronic nose, and the 2-D and 3-D AromaMaps produced by the Aromascan product are referred to herein generically as "multi-dimensional maps." A multi-dimensional map can also have additional dimensions. The neural network feature of the Aromascan product was not used in the examples above, but may be used to improve the accuracy of the results.

Other, non-pulmonary diseases which are known to be identifiable by the smell of a patient's breath, such as diabetes, liver disease, etc. are also detectable utilizing the present invention. The present invention is also applicable for the detection of failure or deterioration in organs and/or other tissue and may also be used for detecting the presence of cancer and other such diseases.

REFERENCES

The references cited below are incorporated herein by reference.

1. Hanson CW, Steinberger HA: Anesthesiology 1997;87:A269

2. Parry AD, et al: Leg ulcer odor detection identifies beta-haemolytic streptococcal infection. Journal of Wound Care. 1995; 4:404-6

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of detecting the presence of a pulmonary pathologic process in a lung of a mammal, the method comprising:

(a) applying a sample of exhaled gas collected from the lung of a mammal to an electronic nose, the electronic nose having a sensor output signal; and (b) analyzing the sensor output signal to determine whether a pulmonary pathologic process is present in the lung of the mammal.

2. A method according to claim 1 wherein step (a) comprises applying the sample of exhaled gas to an electronic nose having a sensor element formed by an array of conducting polymers which have an electrical property that varies according to exposure to gases or vapors.

3. A method according to claim 2 wherein step (b) includes storing reference electrical property variation characteristics and comparing the reference electrical property variation characteristic with the variation in electrical property characteristics of the conducting polymers in the presence of the sample of exhaled gas.

4. A method according to claim 3 wherein the electrical property is impedance.

5. A method according to claim 4 wherein the mammal is a human.

6. A method according to claim 2 wherein the mammal is a human.

7. A method according to claim 1 wherein the analyzing step (b) includes:

(i) representing sensor output signals for a plurality of samples of exhaled gas on a multi-dimensional map, (ii) defining clusters on the map which represent areas of a likely pulmonary pathologic process, and (iii) locating the sensor output signal for a sample of exhaled gas on the map, and determining from the location on the map whether a pulmonary pathologic process exists in the sample.

8. A method according to claim 7 wherein the mammal is a human.

9. A method according to claim 7 wherein the multi-dimensional map is a PCA map.

10. A method according to claim 7 wherein the multi-dimensional map is a Sammon map.

11. A method according to claim 1 further comprising:
   (c) prior to step (a), collecting a sample of exhaled gas from a ventilator which is in fluid communication with the lung of a mammal, the collected sample being used in step (a).

12. A method according to claim 11 wherein the mammal is a human.

13. A method according to claim 1 wherein the pulmonary pathologic process is a lung infection.

14. A method according to claim 13 wherein the mammal is a human.

15. A method according to claim 1 wherein the mammal is a human.

16. A method of detecting the presence of a lung infection in a mammal, the method comprising:
   (a) applying a sample of exhaled gas collected from the lung of a mammal to an electronic nose, the electronic nose having a sensor output signal; and
   (b) analyzing the sensor output signal to determine whether a lung infection is present in the mammal.

17. A method according to claim 16 wherein step (a) comprises applying the sample of exhaled gas to an electronic nose having a sensor element formed by an array of conducting polymers which have an electrical property that varies according to exposure to gases or vapors.

18. A method according to claim 17 wherein step (b) includes storing reference electrical property variation characteristics and comparing the reference electrical property variation characteristic with the variation in electrical property characteristics of the conducting polymers in the presence of the sample of exhaled gas.

19. A method according to claim 18 wherein the electrical property is impedance.

20. A method according to claim 19 wherein the mammal is a human.

21. A method according to claim 17 wherein the mammal is a human.

22. A method according to claim 16 wherein the analyzing step (b) includes:
   (i) representing sensor output signals for a plurality of samples of exhaled gas on a multi-dimensional map,
   (ii) defining clusters on the map which represent areas of a likely pathologic process, and
   (iii) locating the sensor output signal for a sample of exhaled gas on the map, and determining from the location on the map whether a lung infection exists in the sample.

23. A method according to claim 22 wherein the mammal is a human.

24. A method according to claim 22 wherein the multi-dimensional map is a PCA map.

25. A method according to claim 22 wherein the multi-dimensional map is a Sammon map.

26. A method according to claim 16 further comprising:
   (c) prior to step (a), collecting a sample of exhaled gas from a ventilator which is in fluid communication with the lung of a mammal, the collected sample being used in step (a).

27. A method according to claim 26 wherein the mammal is a human.

28. A method according to claim 16 wherein the mammal is a human.

* * * * *